United States Patent
Yoshimura et al.

(10) Patent No.: US 8,466,326 B2
(45) Date of Patent: Jun. 18, 2013

(54) PRODUCTION METHOD FOR UBIQUINONE POWDER FOR USE IN PREPARATIONS AND PRODUCT THEREOF

(75) Inventors: Takafumi Yoshimura, Niigata (JP); Rieko Nakano, Niigata (JP); Masayuki Furutani, Niigata (JP); Takeshi Uchiho, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 38 days.

(21) Appl. No.: 13/260,147

(22) PCT Filed: Mar. 29, 2010

(86) PCT No.: PCT/JP2010/055612
§ 371 (c)(1),
(2), (4) Date: Nov. 14, 2011

(87) PCT Pub. No.: WO2010/113900
PCT Pub. Date: Oct. 7, 2010

(65) Prior Publication Data
US 2012/0059194 A1    Mar. 8, 2012

(30) Foreign Application Priority Data

Mar. 31, 2009 (JP) ................................ 2009-087424
Mar. 31, 2009 (JP) ................................ 2009-087425

(51) Int. Cl.
*C07C 43/23* (2006.01)
*C07C 49/84* (2006.01)
*B28B 17/00* (2006.01)
*A61K 38/43* (2006.01)

(52) U.S. Cl.
USPC ........................... 568/377; 568/662; 424/486

(58) Field of Classification Search
USPC ................... 568/377, 662; 424/486; 264/140
See application file for complete search history.

(56) References Cited

U.S. PATENT DOCUMENTS

| | | |
|---|---|---|
| 2005/0074860 A1 | 4/2005 | Ueda et al. |
| 2007/0053985 A1 | 3/2007 | Ueda et al. |
| 2007/0258967 A1 | 11/2007 | Ueda et al. |
| 2010/0004473 A1 | 1/2010 | Kanaya et al. |

FOREIGN PATENT DOCUMENTS

| | | |
|---|---|---|
| EP | 1 415 969 A1 | 5/2004 |
| EP | 1 666 445 A1 | 6/2006 |
| JP | 2006 213601 | 8/2006 |
| JP | 2007 084532 | 4/2007 |
| WO | 2005 033054 | 4/2005 |
| WO | WO 2007/128350 A1 | 11/2007 |
| WO | 2008 084828 | 7/2008 |

OTHER PUBLICATIONS

International Search Report issued Apr. 20, 2010 in PCT/JP10/055612 filed Mar. 29, 2010.
Extended European Search Report issued Nov. 16, 2012 in Patent Application No. 10758671.1.
Office Action issued Oct. 9, 2012, in Chinese Patent Application No. 201080014749.1.

*Primary Examiner* — Sikarl Witherspoon
(74) *Attorney, Agent, or Firm* — Oblon, Spivak, McClelland, Maier & Neustadt, L.L.P.

(57) ABSTRACT

Disclosed are a production method for a ubiquinone powder for use in preparations, including Step 1 of compression molding a ubiquinone crystal powder at a linear molding pressure of from 0.6 to 2.5 tons/cm to obtain a compressed fragment; and Step 2 of grinding the compressed fragment obtained in Step 1 to obtain a powder; and a ubiquinone powder for use in preparations, which is obtained by the subject production method. According to the subject production method, it becomes possible to provide a ubiquinone powder for use in preparations for medicines and health foods, which has a high bulk density, a small angle of repose and excellent handling properties and fluidity, without using an additive such as an excipient, a binder and the like.

12 Claims, 3 Drawing Sheets

US 8,466,326 B2

PRODUCTION METHOD FOR UBIQUINONE POWDER FOR USE IN PREPARATIONS AND PRODUCT THEREOF

FIELD OF THE INVENTION

The present invention relates to a production method for a ubiquinone powder for use in preparations, which has excellent handling properties and fluidity, and a product thereof. A ubiquinone, especially coenzyme Q10 (hereinafter also referred to as "CoQ10"), is an important material which is widely used in the fields of medicines and health foods.

BACKGROUND ART

A ubiquinone plays an extremely important role as an essential constituent component of the mitochondrial electron transport system on the production of ATP that is a high-energy phosphate compound. Hitherto, for the purpose of activating the myocardial function, CoQ10 has been prescribed as a remedy of congestive heart failure. In recent years, attention to an antioxidative capacity that is another important in vivo action is increasing, and CoQ10 has occupied a very important position in the market of health foods, too.

CoQ10 is a crystalline powder having a melting point of from 50 to 52° C. and can be used as a raw material of medicines and health foods in various product forms such as tablets, hard capsules, soft capsules and the like even as it stands.

However, the crystalline powder of CoQ10 involves such problems in view of preparations concerning handling properties and fluidity that it has a low bulk density and is bulky; and that its aggregation properties and attachment properties are strong. For that reason, there are involved such problems that it is difficult to design and produce capsule preparation products with a high filling factor; and that the production cannot be stably carried out.

Then, for the purpose of solving these problems concerning the production of CoQ10-containing preparations, various technologies have been proposed. For example, there are disclosed a method of mixing a medicine and an additive containing a fluidity modifier such as light anhydrous silicic acid and the like and subsequently grinding the mixture (see, for example, Patent Document 1); a method of granulating a mixed powder containing a low-melting point material and an adsorbing carrier and fluidizing the obtained granulated material at an air supply temperature of a melting point or higher by using a fluidized bed dryer (see, for example, Patent Document 2); and a method of spraying a prolamin protein in a solution state while mixing a CoQ10 powder and an excipient upon being fluidized by a fluidized bed apparatus, thereby obtaining a powder (see, for example, Patent Document 3).

However, all of these methods are those in which the fluidity of the CoQ10 powder is improved by using an additive such as an excipient, a binder and the like, thereby contriving compactification, but they do not at all touch on a technology for improving powder properties of CoQ10 without using an additive.

PRIOR ART DOCUMENTS

[Patent Documents]
  [Patent Document 1] JP-A-2004-123594
  [Patent Document 2] JP-A-2006-160730
  [Patent Document 3] JP-A-2007-191425

SUMMARY OF THE INVENTION

[Problem to be Solved by the Invention]

An object of the present invention is to provide a method for producing a powder for use in preparations for medicines and health foods, which has a high bulk density, small aggregation properties and attachment properties and excellent handling properties and fluidity, and a product thereof.

[Means for Solving the Problem]

In order to solve such a problem, the present inventors made extensive and intensive investigations. As a result, it has been found that a ubiquinone powder for use in preparations, which has small aggregation properties and attachment properties and excellent handling properties and fluidity, can be produced by compression molding a ubiquinone and then grinding it, without using an additive such as a binder, an excipient and the like, leading to accomplishment of the present invention. That is, the present invention is concerned with the following (1) to (12).

(1) A production method for a ubiquinone powder for use in preparations, including Step 1 of compression molding a ubiquinone crystal powder at a linear molding pressure of from 0.6 to 2.5 tons/cm to obtain a compressed fragment; and Step 2 of grinding the compressed fragment obtained in Step 1 to obtain a powder.

(2) The production method for a ubiquinone powder for use in preparations as set forth above in (1), wherein in Step 1, the compression molding is carried out using a roller type compression molding machine.

(3) The production method for a ubiquinone powder for use in preparations as set forth above in (2), wherein in Step 1, the compression molding is carried out by allowing the ubiquinone crystal powder to pass between opposing two rollers having a gap width therebetween of from 0.2 to 1.2 mm.

(4) The production method for a ubiquinone powder for use in preparations as set forth above in any one of (1) to (3), wherein in Step 1, the compression molding is carried out at a product temperature of from 35 to 52° C.

(5) The production method for a ubiquinone powder for use in preparations as set forth above in any one of (1) to (4), including Step 3 of heat treating the powder obtained in Step 2.

(6) The production method for a ubiquinone powder for use in preparations as set forth above in (5), wherein in Step 3, the powder is heat treated at a product temperature of from 30 to 52° C.

(7) The production method for a ubiquinone powder for use in preparations as set forth above in any one of (1) to (6), wherein the ubiquinone is one or more members selected from oxidized CoQ10 and reduced CoQ10.

(8) A ubiquinone powder for use in preparations, which is obtained by the production method as set forth above in any one of (1) to (7).

(9) The ubiquinone powder for use in preparations as set forth above in (8), having a bulk density of from 0.35 to 0.65 g/mL.

(10) The ubiquinone powder for use in preparations as set forth above in (8) or (9), having an angle of repose of from 7 to 30 degrees.

(11) The ubiquinone powder for use in preparations as set forth above in (8), having a bulk density of from 0.4 to 0.65 g/mL.

(12) The ubiquinone powder for use in preparations as set forth above in (8) or (11), having an angle of repose of from 7 to 18 degrees.

[Effect of the Invention]

According to the present invention, it becomes possible to produce and supply a ubiquinone powder for use in preparations exhibiting excellent handling properties and fluidity without using an additive such as an excipient, a binder and the like, and it becomes possible to stably produce preparations of a compact dosage form having a high filling factor, such as capsules and the like.

MODES FOR CARRYING OUT THE INVENTION

Figure 1:
FIG. 1 shows an electron microscopic photograph of a CoQ10 powder for use in preparations, which is obtained by the production method of the present invention. A crystal powder is compressed, whereby taking a laminated structure (magnification: 450 times).

The production method for a ubiquinone powder for use in preparations according to the present invention includes Step 1 of compression molding a ubiquinone crystal powder at a linear molding pressure of from 0.6 to 2.5 tons/cm to obtain a compressed fragment; and Step 2 of grinding the compressed fragment obtained in Step 1 to obtain a powder.

As the ubiquinone which is used in the present invention, there are known ubiquinones which are a derivative of 2,3-dimethoxy-5-methyl-6-polyprenyl-1,4-benzoquinone and in which a number of isoprene units in a side chain thereof is from 6 to 10, and the like. Of these, from the viewpoints of availability and the like, CoQ10 (ubidecanorene) in which a number of isoprene units in a side chain thereof is 10 is preferable. As CoQ10, all of oxidized CoQ10 and reduced CoQ10 can be preferably used.

A production method of the ubiquinone which is used in the present invention is not particularly limited. For example, reduced CoQ10 can be easily synthesized by reducing oxidized CoQ10 with a suitable reducing agent, namely sodium hydrosulfite, vitamin C or the like. For both of oxidized CoQ10 and reduced CoQ10, there can be used a crystal obtained by crystallization or recrystallization. Though the CoQ10 crystal is not always required to be completely dried, from the standpoint of compression moldability, it would be better to remove a solvent as far as possible.

Examples of the compression molding method which can be adopted in Step 1 of the present invention include a roller compression molding method of rotating two rollers and supplying the powder in a gap between the rollers to undergo compression; a tableting method of filling the powder in a die and compressing it; and the like. Of these, a roller compression molding method of undergoing compression molding using a roller type compression molding machine such as a roller compactor and the like is preferable in view of the fact that a compressed fragment with less compression unevenness can be efficiently produced.

A molding pressure at the time of compression molding of Step 1 may be a pressure under which a compressed fragment having been thoroughly compression molded is obtained, and a linear molding pressure in the roller compression molding method is from 0.6 to 2.5 tons/cm, and preferably from 1.0 to 2.0 tons/cm. In the case where the linear molding pressure is higher than 2.5 tons/cm, since a melting point of the ubiquinone is low, there may be the case where a molded product is melted. Also, when the linear molding pressure is a pressure lower than 0.6 tons/cm, molding is so insufficient that a powdering rate in the subsequent grinding step becomes high, whereby a yield of the desired powder tends to become worse.

At the compression molding of Step 1, the raw material powder may be supplied while being preliminarily deaerated for the purpose of increasing the bulk density thereof. A gap between rollers at the time of compression molding is preferably in the range of from 0.2 to 1.2 mm, and more preferably in the range of from 0.4 to 1.0 mm. When the gap between rollers is 0.2 mm or more, a treatment amount is enhanced. Even when the gap between rollers is narrower than 0.2 mm, the production is possible; however, the treatment amount is extraordinarily lowered, so that it becomes an unreal treatment amount. When the gap between rollers is not more than 1.2 mm, the molding pressure can be thoroughly transmitted to a central part in a thickness direction of the molded product. In this way, there is hardly caused such a problem as a lowering of the yield by an increase of the powdering rate to be caused due to the matter that spots are generated in the inside of the molded product, and molding becomes insufficient in the subsequent grinding step.

With respect to a product temperature of the ubiquinone at the time of compression molding of Step 1, it is preferable to keep the product temperature within the range of from 35 to 52° C.; it is more preferable to keep the product temperature within the range of from 36 to 49° C.; and it is still more preferable to keep the product temperature within the range of from 40 to 49° C. When the product temperature exceeds 52° C., it becomes difficult to carry out a stable operation due to contamination on the roller surface by melting of the ubiquinone. Also, when the product temperature is lower than 35° C., a satisfactory compression molded product is not obtainable.

The grinding method which is carried out in Step 2 of the present invention is not particularly limited, and an industrially utilized general grinding method can be adopted. Specifically, there is exemplified a grinding method using a grinder such as a hammer mill, a pin mill, a ball mill, a jet mill and the like. In the case where the compression molded product to be subjected to grinding is large, the foregoing grinding can be carried out after carrying out coarse grinding. Also, for the purpose of removing heat generated by grinding, the grinding can also be carried out while cooling a grinder or a raw material supplying portion, or in liquid nitrogen or in the coexistence of dry ice.

Though the ground product obtained in Step 2 can be used as a powder for use in preparations even as it stands, it can be used after being graded with a sieve having an appropriate opening depending upon the purpose. In the case where a solvent or water remains in the ground product, the ground product can also be used after being dried. Also, in the case where the raw material is a reduced ubiquinone, it easily returns into an oxidized ubiquinone by oxygen in air, and therefore, in order to reduce such a matter, the whole of steps including from compression molding to grinding can also be carried out in an inert atmosphere.

It is preferable that the method of the present invention includes Step 3 of heat treating the powder obtained in Step 2. By carrying out the heat treatment, an angle of repose of the ubiquinone powder for use in preparations can be more reduced.

Though the ground product obtained in Step 2 can be subjected to the heat treatment of Step 3 as it stands, it may also be subjected to the heat treatment after being graded with a sieve having an appropriate opening.

With respect to a heat treatment temperature in Step 3, the heat treatment is required to be carried out at not higher than a melting point of the ubiquinone. The heat treatment temperature is preferably from 30 to 52° C., and more preferably from 40 to 49° C. Though the operation may be possible even at not higher than 30° C., it takes a very long period of time for the heat treatment because of a low temperature, and hence, such is not practical.

A method for the heat treatment in Step 3 is not particularly limited, and in the case of a small amount as in a laboratory scale, the heat treatment may be carried out even in a stationary state. On the supposition that the heat treatment is carried out on an industrial scale, from the viewpoint of shortening the treatment time, it is preferable to carry out the heat treatment while allowing a material to be treated to move. As a measure for allowing the material to be treated to move, there can be specifically adopted a general mixing method such as stirring, vibration or shaking of the material to be treated in a heating state, and the like. Also, the treatment may be carried out in an inert atmosphere of nitrogen or the like. In the case where a solvent or water remains in the ground product obtained in Step 2, the heat treatment can be carried out after drying.

The heat treatment time in Step 3 varies depending upon the treatment temperature or method, and therefore, it cannot be unequivocally limited.

In the treated product obtained in Step 3, there may be the case where small particles fuse with each other by the heat treatment, and therefore, if desired, the treated product obtained in Step 3 may be subjected to coarse grinding or grading with a sieve.

Figure 2:
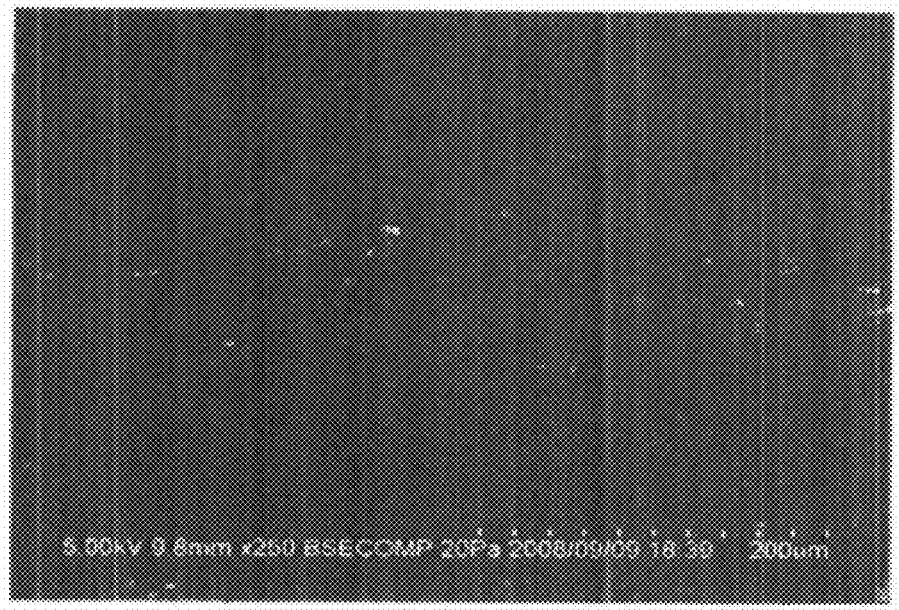
FIG. 2 shows an electron microscopic photograph of a dry crystal powder of a raw material, whereby taking a structure in which a lamellar crystal powder is scattered at random (magnification: 250 times).

A microscopic photograph (FIG. 1) of a powder obtained according to the present invention is shown along with a photograph (FIG. 2) of a raw material crystal powder. As is clear from the photographs, it is noted that a particle of the powder obtained according to the present invention takes a laminated structure in which each and every one of the raw material crystal powders is compressed.

Figure 3:
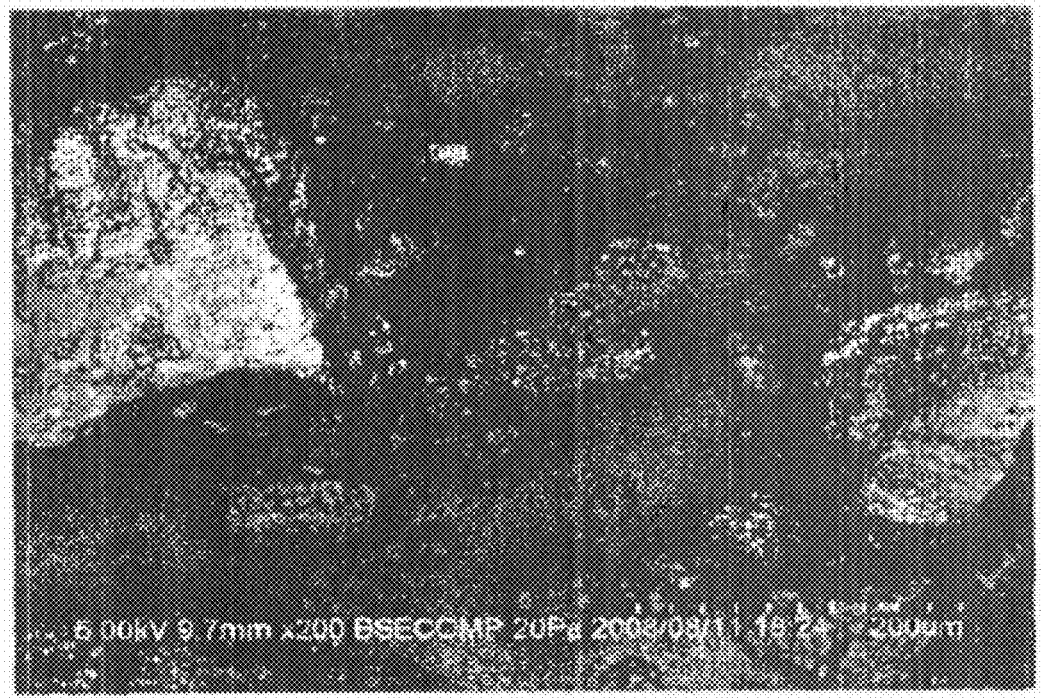
FIG. 3 shows an electron microscopic photograph of a CoQ10 powder for use in preparations before a heat treatment. A crystal powder is compressed, whereby taking a laminated structure.
Figure 4:
FIG. 4 shows an electron microscopic photograph of a CoQ10 powder for use in preparations, having been heat treated at 40° C. for 7 hours.
Figure 5:
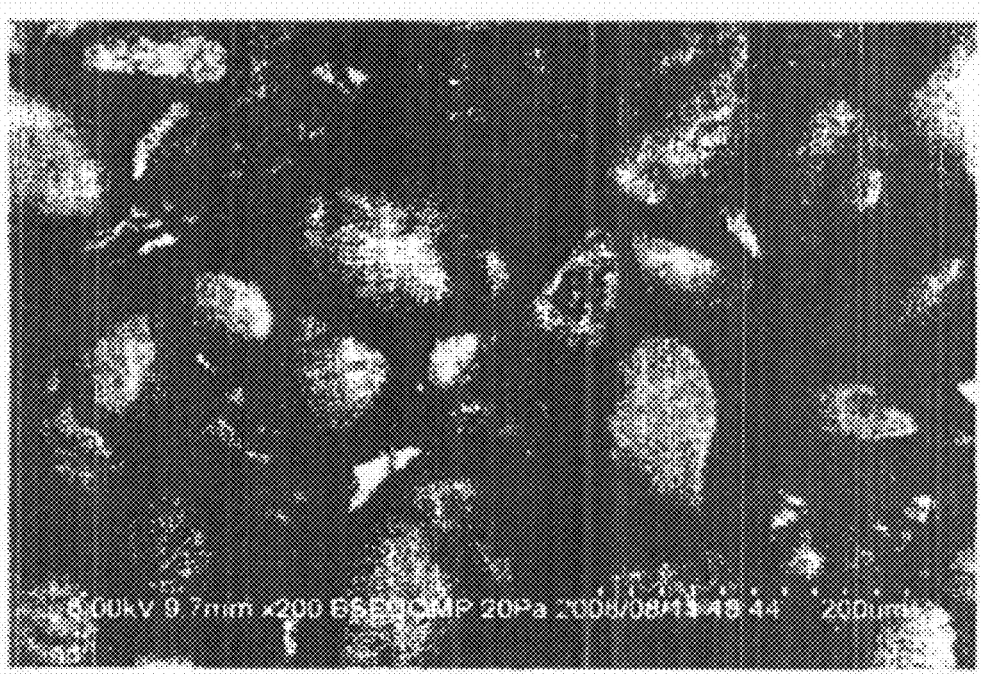
FIG. 5 shows an electron microscopic photograph of a CoQ10 powder for use in preparations, having been heat treated at 40° C. for 28 hours. A state in which a particle becomes round with a lapse of time, and furthermore, the surface thereof is melted is noted.

A photograph of a powder before the heat treatment (FIG. 3); the case where the heat treatment is carried out at a temperature of 40° C. for a time of 7 hours (FIG. 4); and the case where the heat treatment is carried out at a temperature of 40° C. for a time of 28 hours (FIG. 5) are shown. As is clear from the photographs, the particle of the powder obtained by the heat treatment takes a pebble-like form in which the surface thereof is melted.

According to the method of the present invention, a powder having a bulk density of from 0.35 to 0.6 g/mL can be obtained. Furthermore, according to the method of the present invention, a high-bulk density powder having a bulk density of from 0.35 to 0.65 g/mL, and furthermore from 0.4 to 0.65 g/mL can be obtained. In the ubiquinone powder for use in preparations obtained by the method of the present invention, the content per tablet of capsule of the same volume can be made high as compared with that of a low-bulk density product of raw material. Therefore, the capsule can be designed small, so that it is possible to make an oral intake easy.

Also, according to the method of the present invention, a powder having an angle of repose of from 15 to 30 degrees, and furthermore from 7 to 30 degrees can be obtained. Also, a powder having an angle of repose of from 7 to 18 degrees can be obtained by going through Steps 1 to 3. In the method of the present invention, since the angle of repose can be reduced, the obtained ubiquinone powder for use in preparations is good in fluidity, and when mixed with oil, the oil slurry is good in fluidity, too. Therefore, the ubiquinone powder can be easily filled in a capsule, and it becomes possible to stably produce a high-density soft capsule in which the content of the ubiquinone per tablet exceeds 400 mg, or the like. Also, by carrying out the heat treatment, since the angle of repose can be more reduced, as is noted from the photographs shown in FIGS. 4 and 5, the shape of the powder is of a pebble-like form, and no gap is present on the surface thereof. Therefore, in particular, when mixed with oil, the fluidity of the oil slurry can be kept over a long period of time.

EXAMPLES

Examples and Comparative Example of the present invention are hereunder described, but it should not be construed that the present invention is limited only to these Examples. A bulk density and an angle of repose of a powder were measured in the following methods.

(1) Bulk Density:

In order to remove secondary particles of about 1 mm formed after classification, a cylindrical stainless steel-made cup (volume (Vc): 36.0 mL, inner diameter: 30 mm) serving as a saucer of powder was placed beneath an upper funnel installed with a sieve having an opening of 425 μm. A test sample was allowed to pass through the sieve and flow down into the cup until an excess of the powder overflowed. An edge of a spatula which was allowed to stand up vertically on the upper surface of the cup and brought into contact therewith was smoothly moved, thereby carefully scraping off the excess of the powder while keeping the spatula vertical for the purpose of preventing compaction or overflow of the powder from the cup. The whole of the sample on the side surface of the cup was removed, and a mass (M3) of the powder was measured to 0.1%. The powder weighed into the cup was transferred into a measuring cylinder having a volume of 50 mL and a minimum scale of 1 mL, and the bottom surface of the measuring cylinder was mechanically tapped from 50 to 60 times per minute. A bulk volume (V) at the time when the bulk volume did not decrease was read to the minimum scale and defined as a tap volume. A bulk density (g/mL) was calculated according to the following equation.

$$\text{Bulk density (g/mL)} = M3\,(g)/V\,(mL)$$

(2) Angle of Repose:

An angle of repose as an index showing fluidity of the powder was measured by an injection method using a repose angle meter (for use in powder) (ASK-01, manufactured by AS ONE Corporation; funnel in conformity with JIS K6911.5.2., height of fall: 90 mm).

Example 1

A dry crystal powder of CoQ10 obtained by means of crystallization was molded using a roller type compression molding machine (TF-MINI model, manufactured by Freund Corporation) under conditions of a roller linear pressure of 0.7 tons/cm, a roller width of 0.8 mm, a roller rotation number of 4 rpm and a product temperature of 36° C., thereby obtaining a compressed fragment. After this compressed fragment was ground by a coffee mill, the obtained ground product was sieved by an 80-mesh sieve in conformity with the standards of the United States Pharmacopeia, and materials having passed through the sieve were gathered to prepare a CoQ10 powder for use in preparations. This powder had a bulk density of 0.48 g/mL and an angle of repose of 23 degrees.

Incidentally, the dry crystal powder of CoQ10 used as a raw material had a bulk density of 0.2 g/mL and an angle of repose of 43 degrees. In this way, a powder having a high bulk density and improved fluidity was obtained by the present invention. The results are shown in Table 1.

Example 2

The same dry crystal powder of CoQ10 as that in Example 1 was molded using a roller type compression molding machine (TF-156, manufactured by Freund Corporation) under conditions of a roller linear pressure of 1.5 tons/cm, a roller width of 0.8 mm, a roller rotation number of 8 rpm and a product temperature of 36° C., thereby obtaining a compressed fragment. After this compressed fragment was ground by a hammer mill, the obtained ground product was sieved by an 80-mesh sieve in conformity with the standards of the United States Pharmacopeia, and materials having passed through the sieve were gathered to prepare a powder for use in preparations. This powder had a bulk density of 0.5 g/mL and an angle of repose of 20 degrees. The results are shown in Table 1.

Example 3

The same dry crystal powder of CoQ10 as that in Example 1 was molded using a roller type compression molding machine (WP-160x60, manufactured by Turbo Kogyo Co., Ltd.) under conditions of a roller linear pressure of 2.0 tons/cm, a roller width of 0.6 mm, a roller rotation number of 10 rpm and a product temperature of 36° C., thereby obtaining a compressed fragment. This compressed fragment was ground and sieved in the same manner as that in Example 1, thereby preparing a powder for use in preparations. This powder had a bulk density of 0.53 g/mL and an angle of repose of 25 degrees. The results are shown in Table 1.

Example 4

A crystal powder of oxidized CoQ10 (manufactured by oneself) was molded using a roller type compression molding machine, TF-156 (manufactured by Freund Corporation) under conditions of a roller linear pressure of 1.5 tons/cm, a roller width of 0.8 mm, a roller rotation number of 8 rpm and a product temperature of 36° C., thereby obtaining a compressed fragment. This compressed fragment was ground by a hammer mill (manufactured by Dalton Co., Ltd.), thereby obtaining a ground powder. Subsequently, this ground powder was subjected to a stirring treatment by heating under a temperature condition of 40° C. for 28 hours by a universal mixer, EM25B (manufactured by Tsukishima Kikai Co., Ltd.). The obtained treated powder was sieved by an 80-mesh sieve in conformity with the standards of the United States Pharmacopeia, thereby obtaining an oxidized CoQ10 powder. This powder had a bulk density of 0.56 g/mL and an angle of repose of 10 degrees.

Example 5

60 g of the CoQ10 powder for use in preparations obtained in Example 1 was charged into a 300-mL jacketed flat bottom flask and heat treated at 40° C. for 24 hours while stirring by a stirring blade having a four-blade propeller shape. The obtained powder had a bulk density of 0.54 g/mL and an angle of repose of 15 degrees.

Coparative Example 1

The same dry crystal powder of CoQ10 as that in Example 1 was molded using a roller type compression molding machine (WP-160x60, manufactured by Turbo Kogyo Co., Ltd.) under conditions of a roller linear pressure of 3.0 tons/cm, a roller width of 0.6 mm, a roller rotation number of 5 rpm and a product temperature of 36° C. However, a melted material attached onto the roller surface, whereby a compressed fragment was not obtained. The results are shown in Table 1.

TABLE 1

| Example | Roller linear pressure (ton/cm) | Roller width (mm) | Roller rotation number (rpm) | Presence or absence of heat treatment | Bulk density (g/mL) | Angle of repose (degree) |
|---|---|---|---|---|---|---|
| Raw material crystal | — | — | — | — | 0.2 | 43 |
| Example 1 | 0.7 | 0.8 | 4 | No | 0.48 | 23 |
| Example 2 | 1.5 | 0.8 | 8 | No | 0.5 | 20 |
| Example 3 | 2.0 | 0.6 | 10 | No | 0.53 | 25 |
| Example 4 | 1.5 | 0.8 | 8 | Yes | 0.56 | 10 |
| Example 5 | 0.7 | 0.8 | 8 | Yes | 0.54 | 15 |
| Comparative Example 1 | 3.0 | 0.6 | 5 | — | — | — |

[Industrial Applicability]

According to the present invention, it is possible to produce a ubiquinone powder for use in preparations, which has a high bulk density, a small angle of repose and excellent handling properties and fluidity, without using an additive such as an excipient, a binder and the like; and it becomes possible to provide a ubiquinone powder for use in preparations for medicines and health foods.

The invention claimed is:

1. A method for producing a ubiquinone powder, comprising:
    a) compression molding a ubiquinone crystal powder at a linear molding pressure of from 0.6 to 2.5 tons/cm to obtain a compressed fragment; and
    b) grinding the compressed fragment to obtain a powder.
2. The method of claim 1, wherein the compression molding a) is carried out using a roller type compression molding machine.
3. The method of claim 2, wherein the compression molding a) is carried out by allowing the ubiquinone crystal powder to pass between two opposing rollers having a gap width therebetween of from 0.2 to 1.2 mm.
4. The method of claim 1, wherein the compression molding a) is carried out at a product temperature of from 35 to 52° C.
5. The method of claim 1, further comprising:
    c) heat treating the powder obtained in Step b).
6. The method of claim 5, wherein the heat treating c) is at a product temperature of from 30 to 52° C.
7. The method of claim 1, wherein the ubiquinone is at least one selected from the group consisting of oxidized CoQ10 and reduced CoQ10.
8. A ubiquinone powder obtained by the method of claim 1.
9. The ubiquinone powder of claim 8 with a bulk density of from 0.35 to 0.65 g/mL.

10. The ubiquinone powder of claim 8 with an angle of repose of from 7 to 30 degrees.

11. The ubiquinone powder of claim 8 with a bulk density of from 0.4 to 0.65 g/mL.

12. The ubiquinone powder of claim 8 with an angle of repose of from 7 to 18 degrees.

\* \* \* \* \*